(12) United States Patent
Denkovich

(10) Patent No.: US 11,806,508 B1
(45) Date of Patent: Nov. 7, 2023

(54) FIXTURE FOR FILLING HYPODERMIC SYRINGES

(71) Applicant: Dennis Denkovich, Rochester, PA (US)

(72) Inventor: Dennis Denkovich, Rochester, PA (US)

(*) Notice: Subject to any disclaimer, the term of this patent is extended or adjusted under 35 U.S.C. 154(b) by 359 days.

(21) Appl. No.: 17/087,583

(22) Filed: Nov. 2, 2020

(51) Int. Cl.
*A61M 5/178* (2006.01)
*A61M 5/31* (2006.01)

(52) U.S. Cl.
CPC ........ *A61M 5/1782* (2013.01); *A61M 5/3137* (2013.01); *A61M 2005/3114* (2013.01); *A61M 2209/045* (2013.01); *A61M 2209/084* (2013.01)

(58) Field of Classification Search
CPC .............. A61M 5/1782; A61M 5/3137; A61M 5/3129; A61M 5/31; A61M 2005/3114; A61M 2209/045; A61M 2209/084
See application file for complete search history.

(56) References Cited

U.S. PATENT DOCUMENTS

| 3,661,189 | A | * | 5/1972 | Bowser | A61M 5/1782 141/378 |
| 5,056,744 | A | * | 10/1991 | Ludwig | A61J 1/2096 248/154 |
| 9,610,221 | B2 | * | 4/2017 | Stierer | A61J 1/16 |
| 2019/0307644 | A1 | * | 10/2019 | Cancellieri | A61J 1/2006 |

* cited by examiner

*Primary Examiner* — Brandy S Lee
*Assistant Examiner* — Fatimata Sahra Diop
(74) *Attorney, Agent, or Firm* — William F. Lang, IV; LANG PATENT LAW LLC

(57) ABSTRACT

A fixture for filling a hypodermic syringe includes a vial support and a finger flange support that are substantially coplanar with each other. The vial support holds a vial while the needle of a hypodermic syringe is inserted through the top of the vial. The syringe is then positioned so that the plunger side of one of the finger flanges engages a finger flange support. The finger flange support resists movement of the syringe while the plunger is withdrawn, filling the barrel of the syringe from the vial. The vial and needle are at least partially supported throughout the filling process.

10 Claims, 11 Drawing Sheets

FIXTURE FOR FILLING HYPODERMIC SYRINGES

TECHNICAL FIELD

The present invention is related to the filling of hypodermic syringes with medication. More specifically, a fixture for holding a medication vial and for supporting the hypodermic syringe is provided.

BACKGROUND INFORMATION

Hypodermic syringes are widely used for administering medication, both by health care professionals, by patients themselves, and by non-medical caregivers for patients. Filling a hypodermic syringe requires inserting the needle into a vial of medication, and withdrawing the plunger from the barrel to draw the medication from the vial into the barrel until the correct dosage of medication is contained within the barrel. Measurement indicia on the barrel show the volume of medication within the barrel.

Filling a hypodermic syringe can be a challenge for those with impaired hand dexterity and/or impaired vision. Elderly patients who are likely to need medication administered by a hypodermic syringe are also likely to have one or both of these disabilities as a result of the aging process, or perhaps as a result of the condition which requires the medication.

Accordingly, there is a need for a fixture for supporting a vial and a hypodermic syringe during filling of the syringe in order to reduce the amount of dexterity required to properly fill the syringe. There is a further need for a fixture for filling a syringe that makes accurate measurement of the dosage easier to perform during filling of the syringe.

SUMMARY

The above needs are met by a fixture for supporting a hypodermic needle and vial. The fixture comprises a fixture support. The fixture further includes a vial support extending from the fixture support. The vial support includes a vial securing device. The fixture also includes a finger flange support extending from the fixture support, with the finger flange support being substantially coplanar with the vial support. A vial may be secured to the vial support. A hypodermic syringe may be inserted into the vial. A plunger side surface of a finger flange on a barrel of the hypodermic syringe may be placed into contact with the finger flange support. The finger flange support resists movement of the barrel while a plunger of the hypodermic syringe is withdrawn to fill the syringe from the vial.

The above needs are also met by a method of filling a hypodermic syringe. The method comprises providing a fixture. The fixture comprises a fixture support; a vial support extending from the fixture support, with the vial support including a vial securing device; and a finger flange support extending from the fixture support, with the finger flange support being substantially coplanar with the vial support. The method further includes securing a vial to the vial support, inserting a needle of a hypodermic syringe into the top of the vial, placing a plunger side surface of a finger flange disposed on a barrel of the hypodermic syringe against the finger flange support, and withdrawing a plunger of the hypodermic syringe to fill the barrel of the syringe with medication.

These and other aspects of the invention will become more apparent through the following description and drawings.

BRIEF DESCRIPTION OF THE DRAWINGS

Like reference characters denote like elements throughout the drawings.

DETAILED DESCRIPTION

Figure 1:
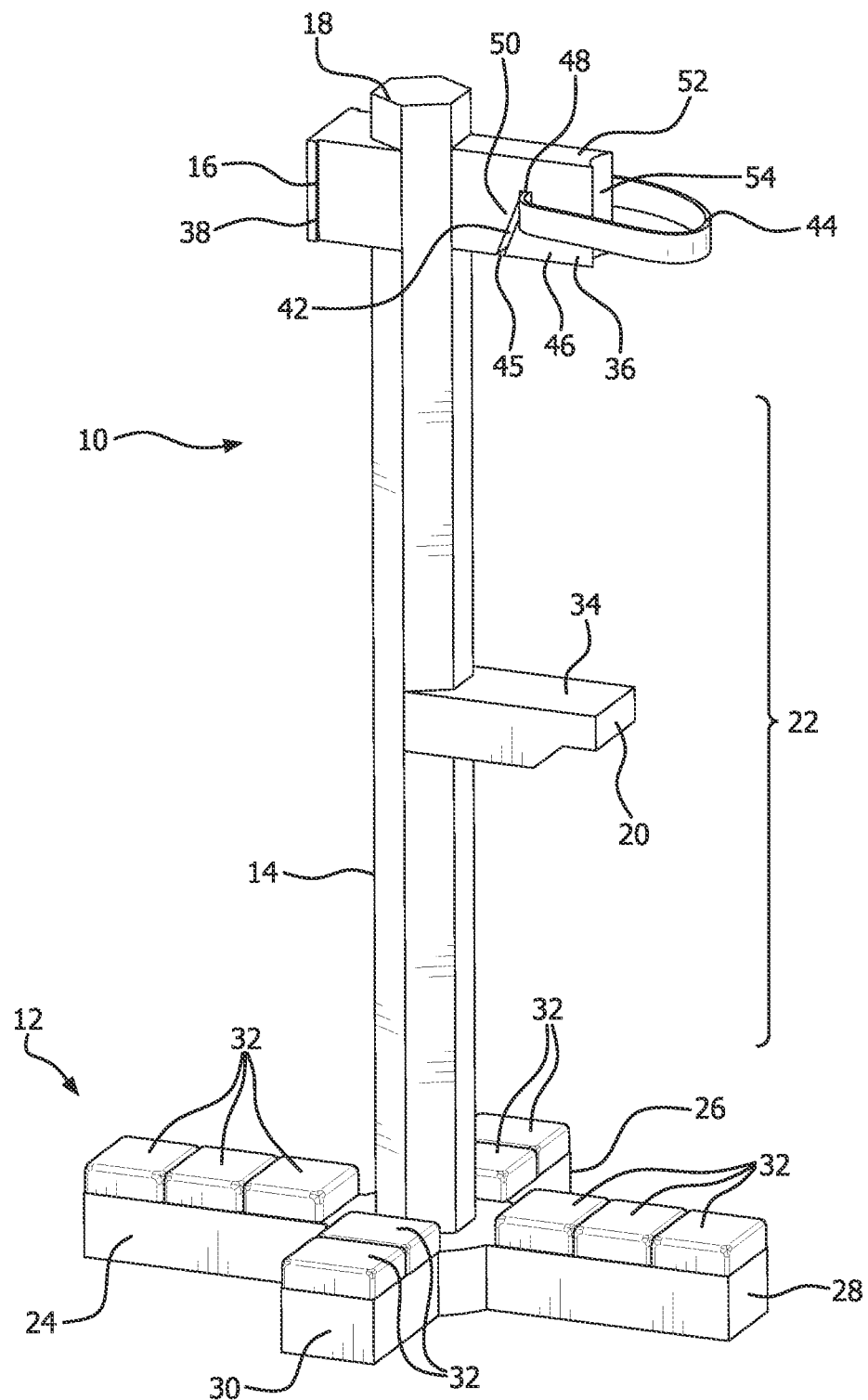
FIG. 1 is a perspective view of a fixture for filling a hypodermic syringe.

Referring to the drawings, a fixture 10 for filling a hypodermic syringe is illustrated. Referring to FIG. 1, the fixture 10 includes a fixture support which in the illustrated example includes a base 12 and a substantially vertical post 14 extending upwardly from the base 12. As used herein, the fixture support is the portion of the fixture that supports the vial support and finger flange support in the desired relationship as described below. A vial support 16 is disposed adjacent to the upper end 18 of the post 14. A finger flange support 20 is disposed on an intermediate portion 22 of the post 14. As explained in greater detail below, some examples of the fixture 10 may include multiple finger flange supports 20, and/or a movable finger flange support 20.

The base 12 may have any configuration that provides sufficient length and width in horizontal directions to support the post 14 in a position that facilitates filling a hypodermic syringe with medication as described below. In the illustrated example, the post 14 is supported in a substantially vertical position. In the example illustrated in FIG. 1, the base 12 includes a plurality of outwardly extending legs, which in the illustrated example includes four legs 24, 26, 28, and 30 extending outward from the post 14 a sufficient distance to properly support the post 14. The legs 24, 26, 28, 30 also have sufficient angular spacing between the legs 24, 26, 28, 30 to. In the illustrated example, weights 32 form a part of each of the posts 24, 26, 28, 30. Support the post 14 in any direction. In the illustrated example, the legs 24 and 28 are substantially collinear with each other, and the legs 26 and 30 are generally collinear with each other. The legs 26 and 30 are substantially perpendicular to the legs 24 and 28. In the illustrated example, the legs 24, 26, 28, 30 are weighted to increase the resistance to undesired movements of the post 14. As used herein, substantially perpendicular or substantially parallel means sufficiently close to perpendicular and parallel to accomplish the purpose of properly supporting the fixture.

The finger flange support 20 extends outward from an intermediate portion 22 of the post 14, and includes a finger flange engaging surface 34 that is substantially perpendicular to the post 14. As used herein, substantially perpendicular to the post means sufficiently perpendicular to provide adequate abutment to the finger flange of a hypodermic syringe to support the syringe as described below. The finger flange support 20 in the illustrated example includes a substantially horizontal top surface 34.

The vial support 16 extends outward from the post 14, adjacent to the upper end 18 of the post 14. The vial support 16 is substantially coplanar with the finger flange support 20. As used herein, substantially coplanar means that sufficiently close to being within the same plane for a hypodermic syringe having a needle inserted into a vial held on the vial support may also have a finger flange supported on the finger flange support, as described below.

Figure 2:
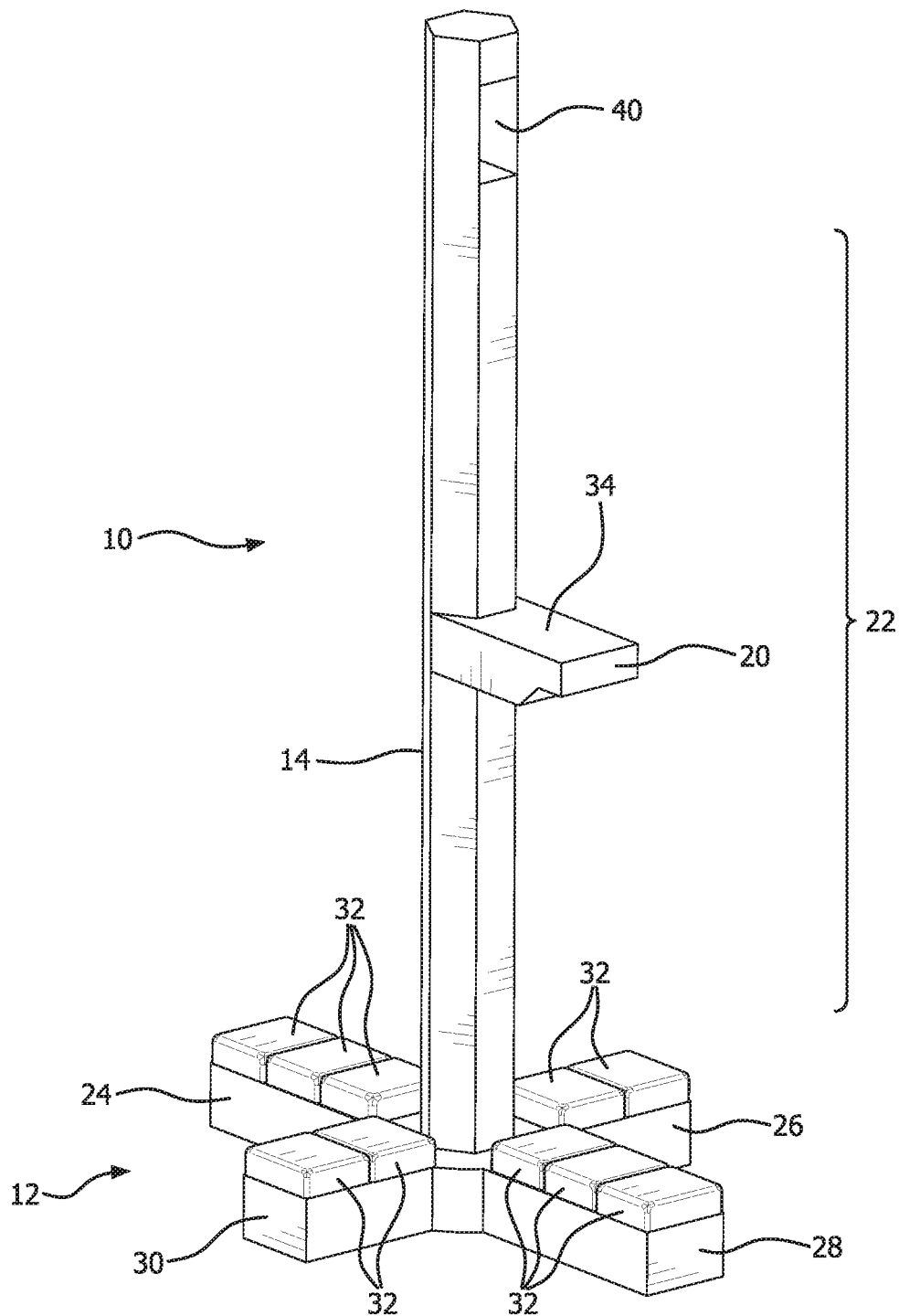
FIG. 2 is a perspective view of a base and vertical support for the fixture of FIG. 1
Figure 3:
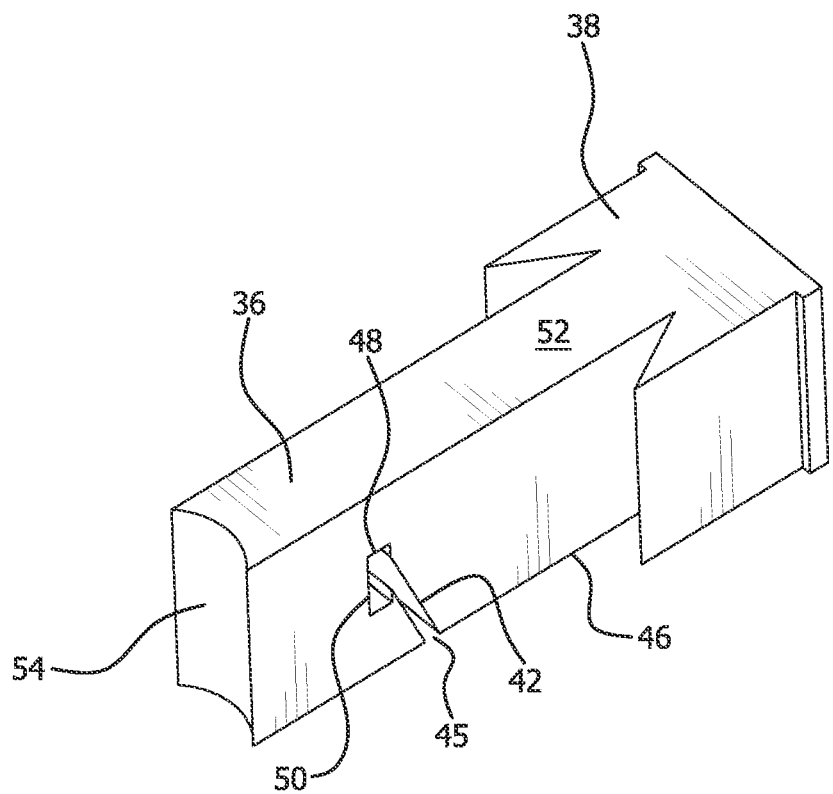
FIG. 3 is a perspective view of a vial support for the fixture of FIG. 1.

Referring to FIGS. 1-3, an example of a vial support 16 is illustrated. The illustrated example of a vial support 16 is removable and replaceable. The support. 20 includes a support arm 36 and a stop 38. The support arm 36 is dimensioned and configured to fit within the hole 40 defined within the post 14. The stop 38 is wider than the arm 36 in at least one direction, so that the stop 38 abuts the post 14 once the support arm 36 has been fully inserted into the hole 40, resisting further insertion of the support arm 36. The vial support 16 includes a vial securing device which is used to fasten a vial to the support arm 36. The illustrated example of the support arm 36 defines a slot 42 for receiving an elastomeric band 44, in the illustrated example, the slot 42 includes an open end 45 which in the illustrated example is disposed on the bottom surface 46 of the support arm 36. The slot 42 also includes a closed end 48 having an enlarged aperture 50 to retain the elastomeric band 44 therein, resisting slippage of the elastic band 44 towards the open end 45 of the slot 42 and permitting pivoting of the elastic band as described below. The first support surface or upper surface 52 of the support arm 36 in the illustrated example is generally flat and substantially perpendicular to the post 14. As used herein, substantially perpendicular to the post means sufficiently close to perpendicular to support a vial during a syringe filling operation as described below. Other examples of the support arm 36 may include a concave first support surface 52. The second support surface 54 of the support arm 36 is disposed on the end of the support arm 36. The second support surface 54 is substantially parallel to the post 14. As used herein, substantially parallel means sufficiently parallel so that a medication vial is supported in a position that enables a hypodermic syringe having its needle inserted into the vial to be supported by the finger flange support as described below. In the illustrated example, the second support surface 54 is concave, defining a shallow channel extending from the bottom surface 46 to the upper surface 52. The radius of the concave surface 54 (and of the surface 52 if the surfaces also concave) may correspond to the typical radius of a typical medicine vial. In other examples, the concave surfaces 52, 54 may have a shallow V-shape to position and support a variety of vial diameters.

Figure 4:
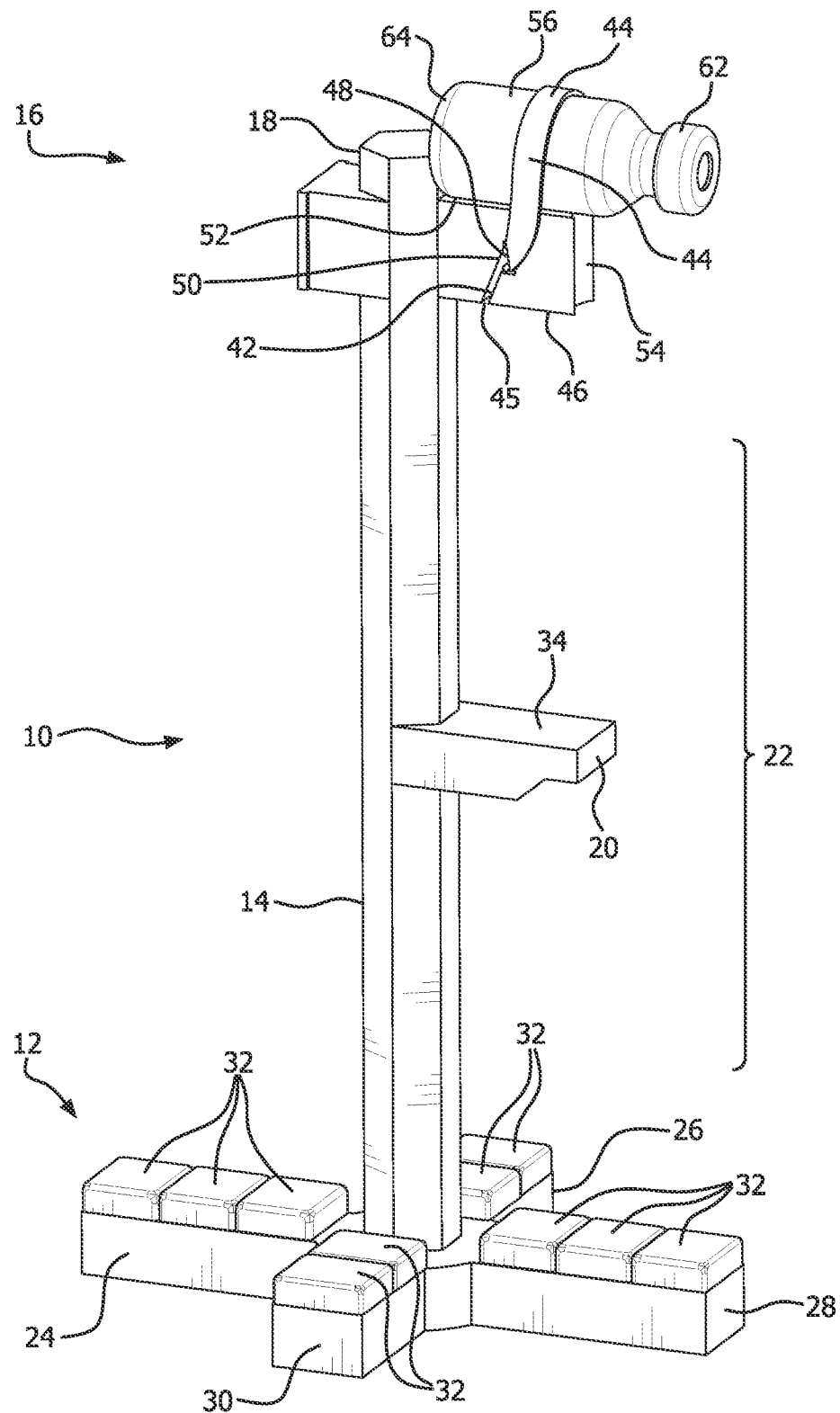
FIG. 4 is a perspective view of the fixture of FIG. 1, showing a vial secured to the vial support.
Figure 5:
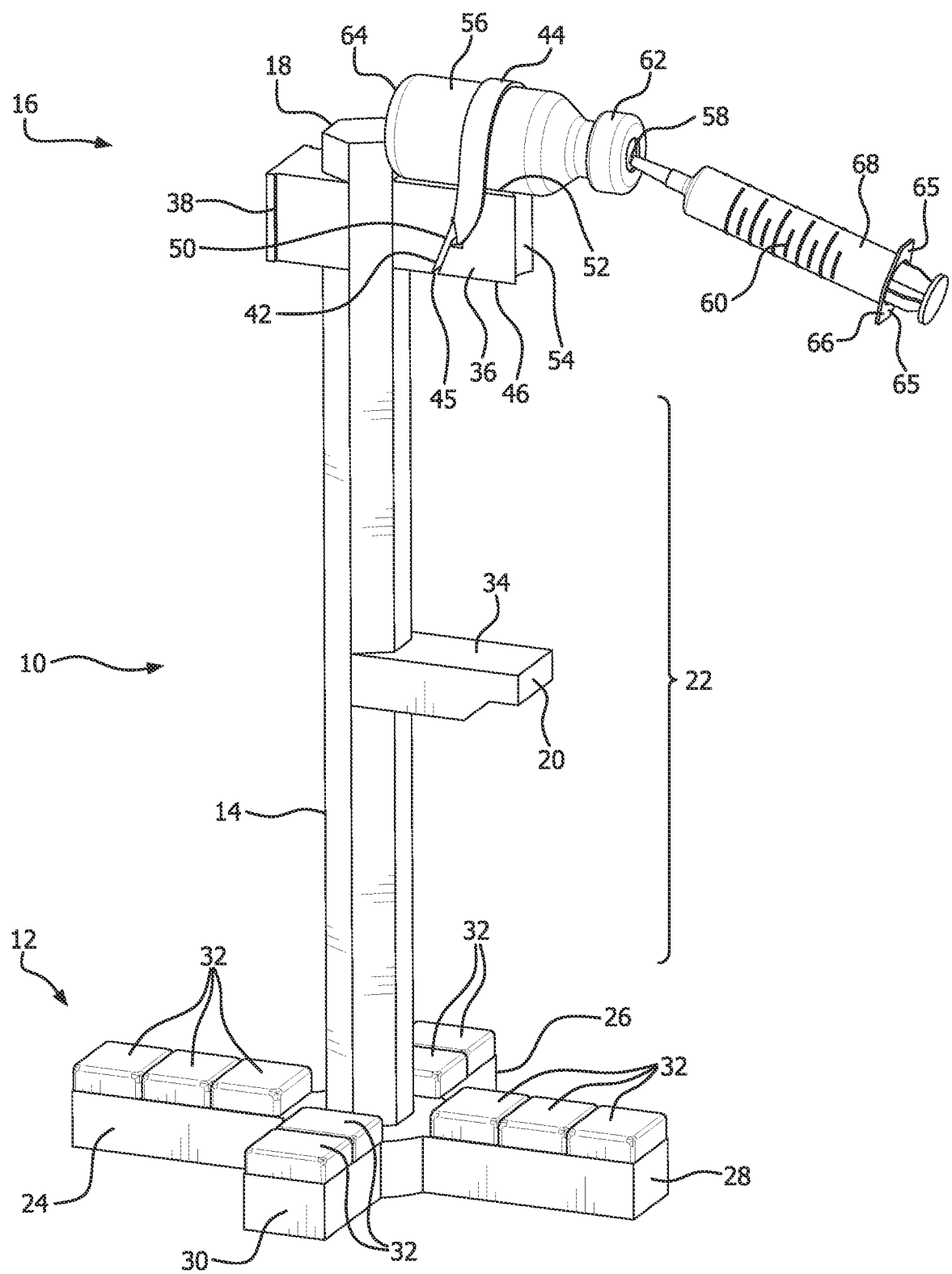
FIG. 5 is a perspective view of the fixture of FIG. 1, showing the needle of a hypodermic syringe inserted into a vial which is secured to the vial support.
Figure 6:
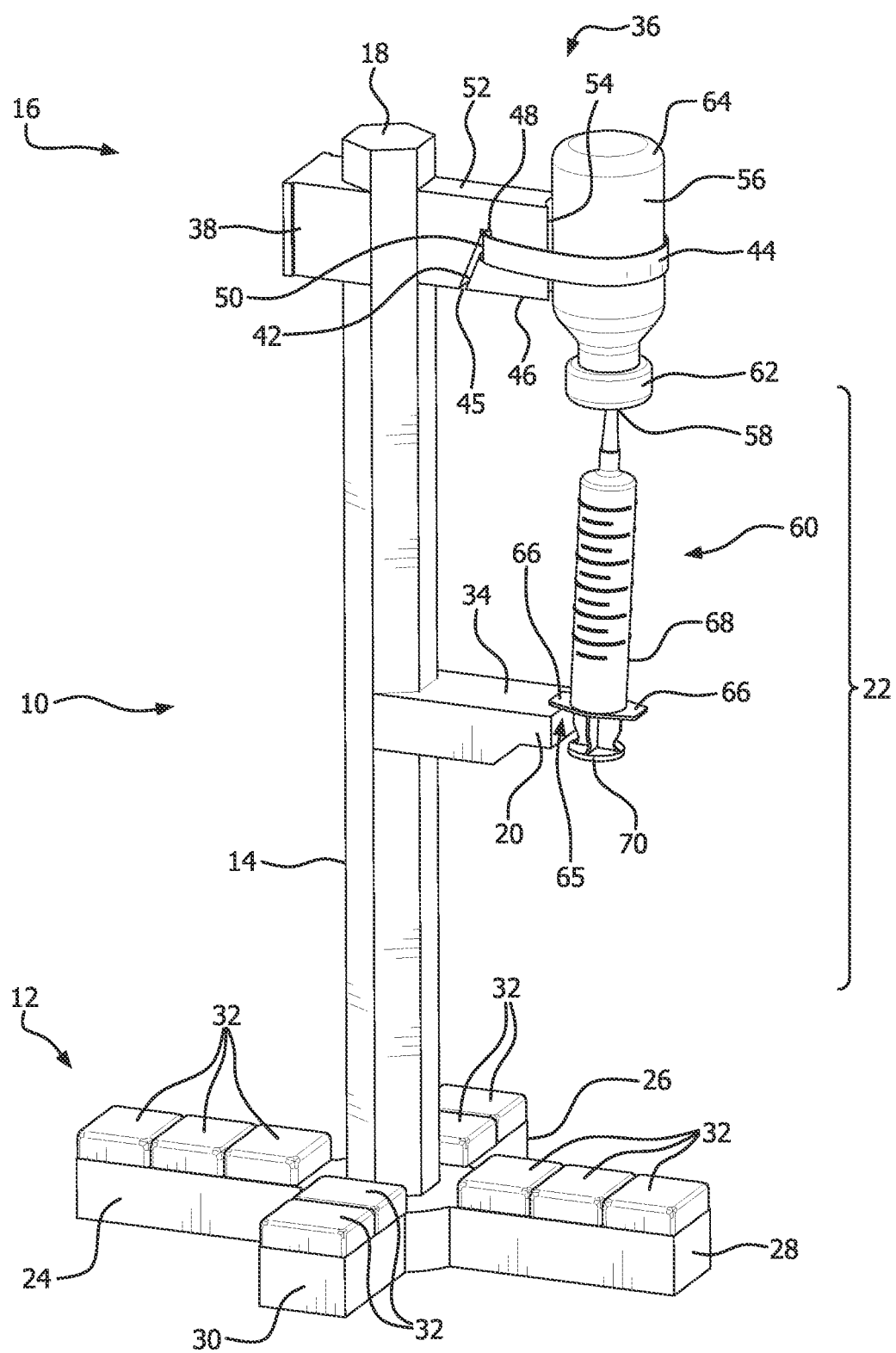
FIG. 6 is a perspective view of the fixture of FIG. 1, showing a vial secured to the vial support in a vertical orientation, and the needle support arm engaging a finger flange of the hypodermic syringe.
Figure 7:
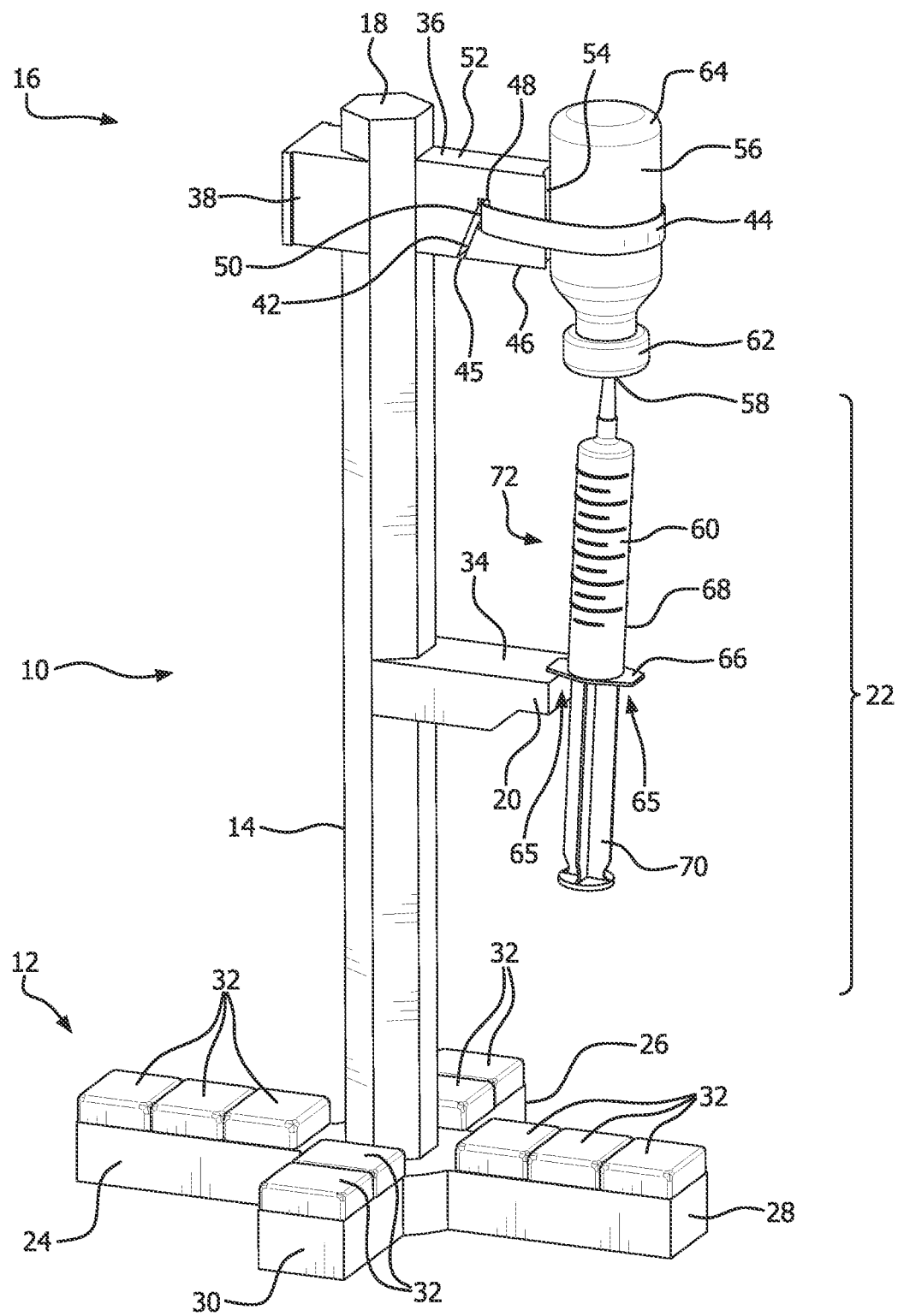
FIG. 7 is a perspective view of the fixture of FIG. 1, showing the plunger of a hypodermic syringe being withdrawn from the barrel of the syringe to withdraw medication from the vial, using the fixture of FIG. 1 to support the vial as well as the finger flange of the syringe.

FIGS. 4-7 illustrate the process of filling a hypodermic syringe using the fixture 10. As shown in FIG. 4, the elastomeric hand 44 is used to secure the vial 56 to the top surface 52 of the vial support 16. The needle 58 of the hypodermic syringe 60 is then inserted through the top 62 of the vial 56, as shown in FIG. 5. The bottom 64 of the vial 56 abuts the top 18 of the post 14, contributing to holding the vial 56 in place as the hypodermic syringe 60 is inserted into the vial 56. The vial 56 and hypodermic syringe 60 are then rotated to the position shown in FIG. 6, with the vial 56 being held against the end surface 54 of the vial support 16 by the elastomeric band 44 which has pivoted around the closed end 48 of the slot 42, With the vial 56 in this position, the plunger side surface 65 of the finger flange 66 formed on the end of the barrel 68 of the hypodermic syringe 60 rests on the top surface 34 of the finger flange support 20. Turning to FIG. 7, with the vial 56 and hypodermic syringe 60 supported in this manner, the plunger 70 of the hypodermic syringe 60 can be withdrawn from the barrel 68 until the indicia 72 provided on the barrel 68 indicates that the correct dosage of medication has been withdrawn from the vial 56 into the barrel 68. The needle 58 of the hypodermic syringe 60 can then be removed from the top 62 of the vial 56, and the medication can then be injected into the patient.

Figure 8:
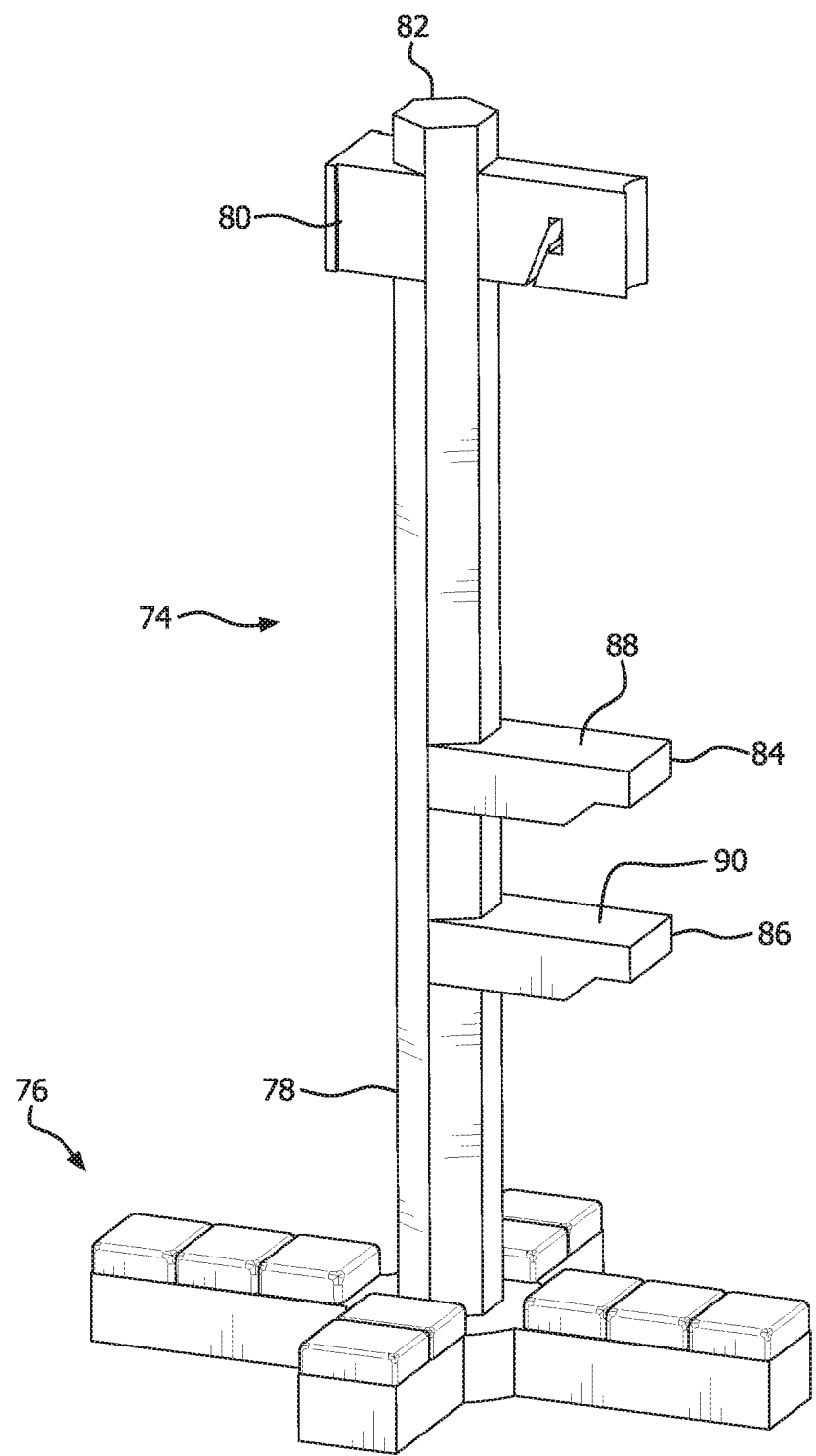
FIG. 8 is a perspective view of another fixture for filling a hypodermic syringe.

FIG. 8 illustrates an alternative fixture 74 having many elements in common with the fixture 10. The fixture 74 includes a base 76 which in the illustrated example is substantially the same as the base 12. A post 78 which in the illustrated example is substantially identical to the vertical post 14 extends from the base 76. A vial support 80 which in the illustrated example is substantially identical to the vial support 16 is disposed adjacent to the upper end 82 of the post 78. A pair of finger flange supports 84, 86 are disposed on an intermediate portion 88 of the post 78. Each of the finger flange supports 84, 86 are substantially identical to the finger flange support 20, and each of the finger flange supports 84, 86 includes a finger flange engaging surface 88, 90, respectively, for supporting the finger flange 66 of a hypodermic syringe 60. The use of the fixture 74 is the same as illustrated in FIGS. 4-7, with the added advantage that hypodermic syringes of two different sizes may be utilized with the fixture 74.

Figure 9:
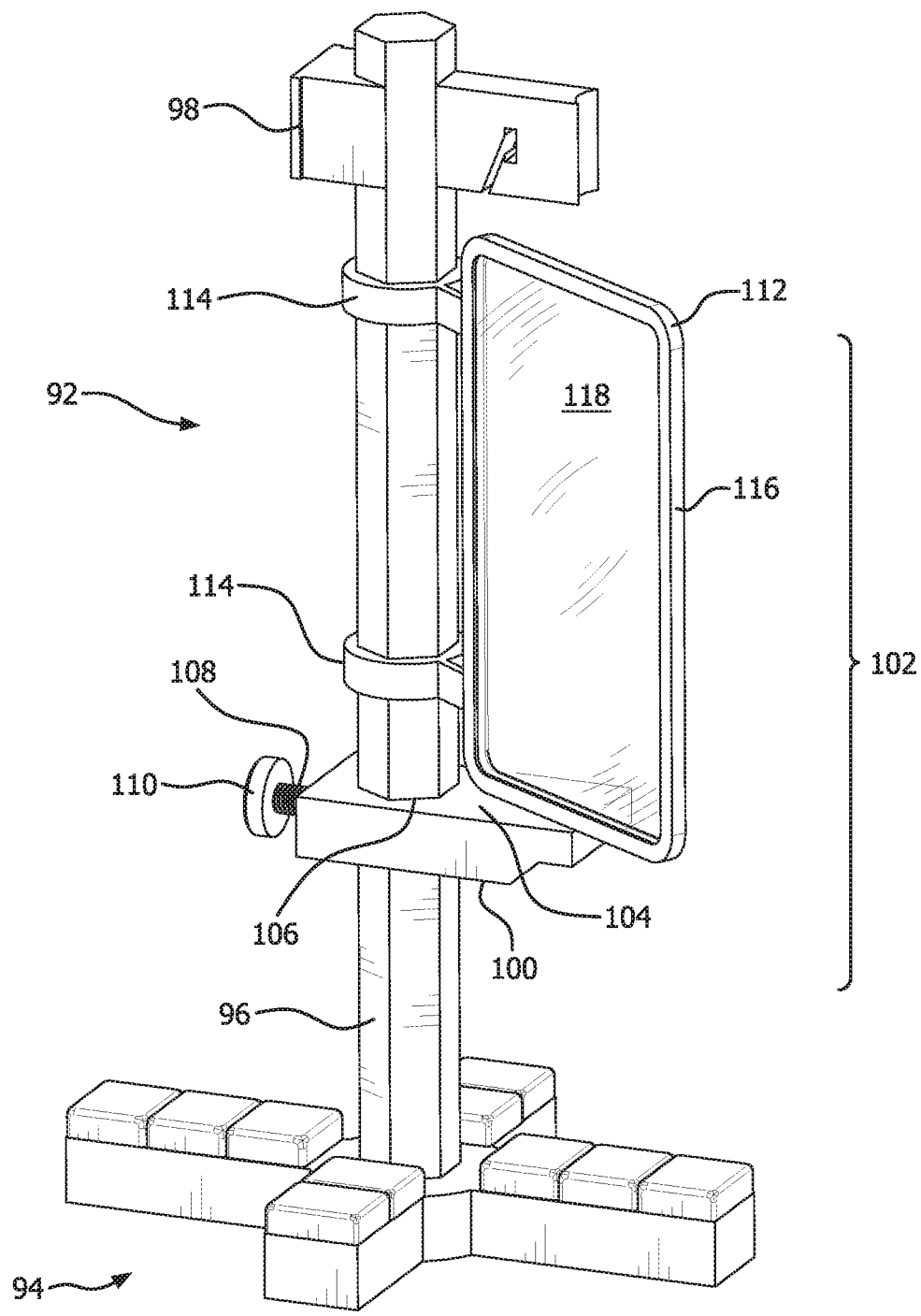
FIG. 9 is a perspective view of yet another fixture for filling a hypodermic syringe.

FIG. 9 illustrates a nut or alternative fixture 92 having many elements in common with the fixtures 10 and 74. The fixture 92 includes a base 94 which in the illustrated example is substantially the same as the base 12. A post 96 which in the illustrated example is substantially identical to the post 14 extends from the base 94. A vial support 98 which in the illustrated example is substantially identical to the vial support 16 is disposed adjacent to the upper end 82 of the post 78. A movable finger flange support 100 is disposed on an intermediate portion 102 of the post 96.

The finger flange support 100 is similar to the finger flange support 20, and includes a top surface 104 for supporting the finger flange 66 of a hypodermic syringe 60. The use of the fixture 74 is the same as illustrated in FIGS. 4-7, with the added advantage that hypodermic syringes of two different sizes may be utilized with the fixture 74. The finger flange support 100 defines an aperture 106 which receives the post 96 therethrough. A securing mechanism in the illustrated example includes a threaded rod 108 that is threadedly secured within the finger flange support 100, and includes a knob 110 at its free end. When tightened, the threaded rod 108 abuts the post 96, securing the post 96 between the threaded rod 108 and the opposite side of the aperture 106. The placement of the finger flange support 100 can thus be adjusted by loosening the threaded rod 108, sliding the finger flange support on the post 96, and then tightening the threaded rod 108 until the finger flange support 100 does not move freely.

The illustrated example of the fixture 92 also includes a magnifier 112 secured thereto. The illustrated example of a magnifier 112 includes a pair of connectors 114 securing the frame 116 of the magnifier 112 to the post 96. The lens 118 is thus positioned to facilitate reading the indicia 72 on the barrel 68 of a hypodermic syringe, as well as observing the amount of medication within the barrel 68 while filling a syringe 60. The connectors 114 may have any form that is known to those skilled in the art, including clamps, straps, posts fitting within apertures defined on the post 96, one-piece construction with the post 96, and the like. The position of the lens 118 may be fixed or movable, again using any means known to those skilled in the art. The magnifier 112 may be used with any example of the fixture for supporting a hypodermic syringe.

Figure 10:
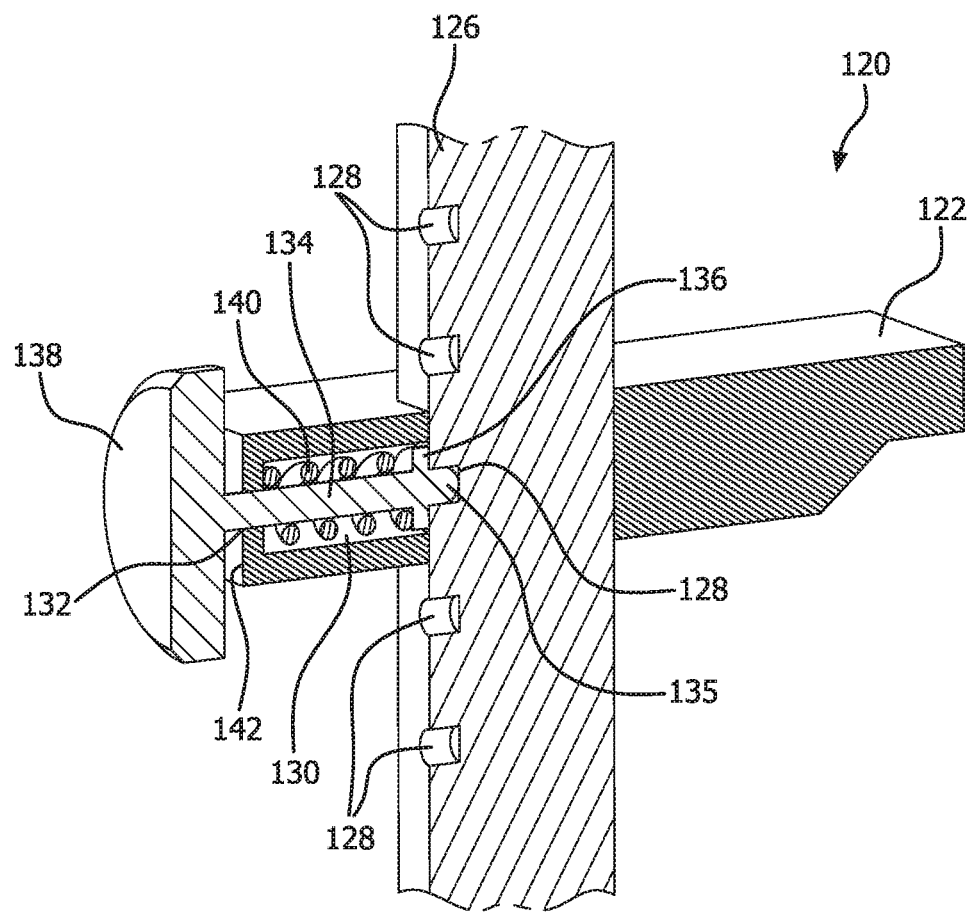
FIG. 10 is a partially cutaway perspective view of an alternative finger flange support for a fixture for filling a hypodermic syringe.

Another example of a securing mechanism for a movable finger flange support 120 is illustrated in FIG. 10. The finger flange support 120 includes a finger flange supporting surface 122, and an aperture 124 for receiving a post 126 of a fixture for supporting a hypodermic needle. The illustrated example of the post 126 includes a plurality of apertures 128 defined therein. The finger flange support 120 includes a hollow portion 130 opposite the surface 122, and an aperture 132. A rod 134 that is dimensioned and configured to fit within the apertures 128 passes through the aperture 132. The rod 134 includes a spring stop 136 at one end, within the hollow portion 130, and a handle 138 at the opposite end. A spring 140 is disposed around the rod 134, between the spring stop 136 and the exterior wall 142 of the finger flange support 120. The spring 140 biases the rod 134 towards the post 126 so that the tip 135 of the rod 134 fits into one of the apertures 128. Retracting the handle 138 removes the rod 134 from the aperture 128, permitting the finger flange support 120 to slide along the post 126. Releasing the handle 134 permits the rod 134 to engage an aperture 128 to secure the finger flange stop 120 in a desired position.

Figure 11:
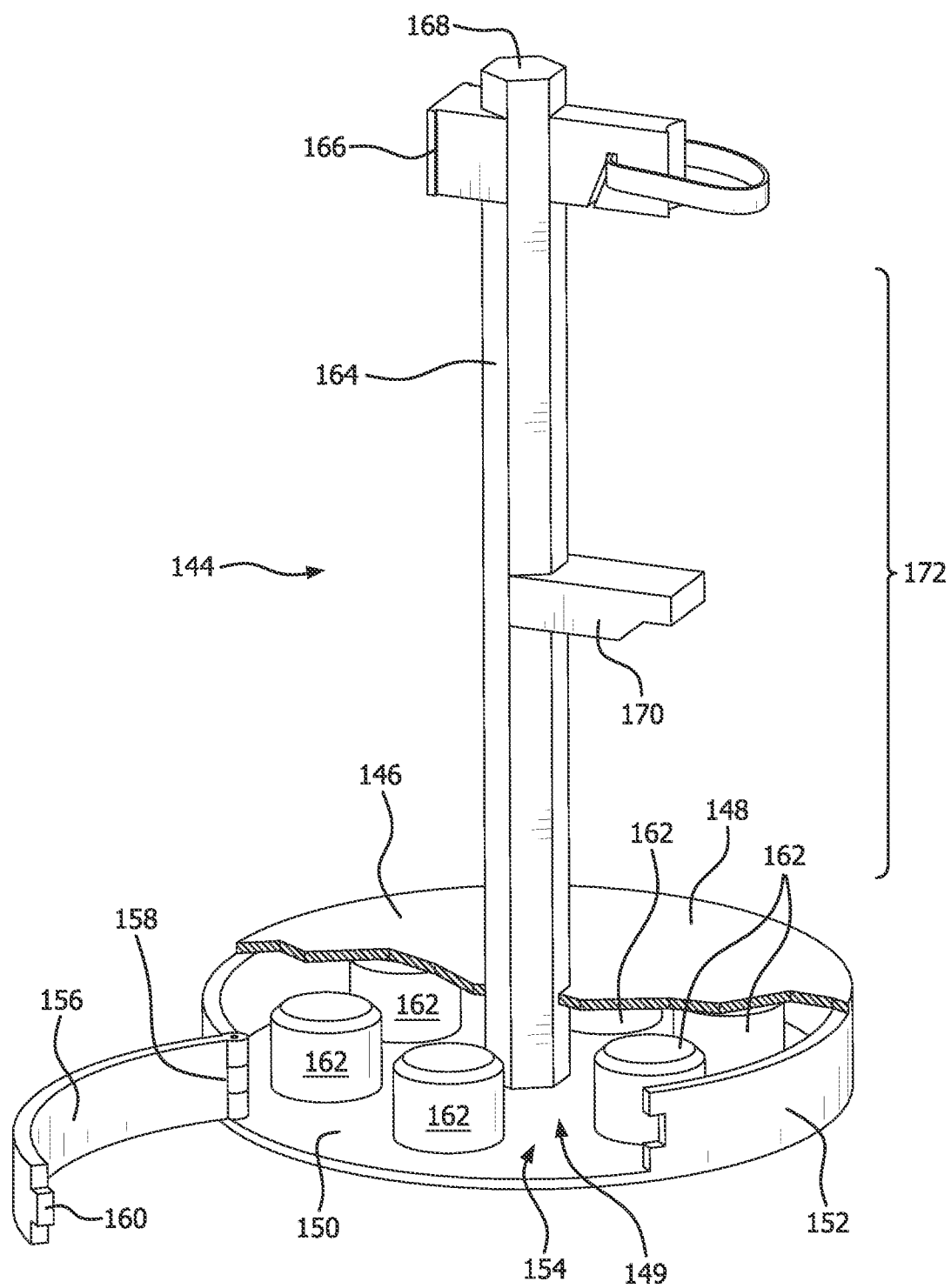
FIG. 11 is a perspective view of yet another fixture for filling a hypodermic syringe.

FIG. 11 illustrates another example of a fixture 144 for supporting a hypodermic syringe. The fixture 144 includes a base 146 which in the illustrated example includes a top wall 148, bottom wall 150, and side wall 152 defining a weight-receiving opening 154. In the illustrated example, the weight-receiving opening 154 can be accessed through a cover 156 that is hingedly secured to the base 146 using the hinge 158, and which includes a latch 160 opposite the hinge 158. Weights 162 may be placed within the weight-receiving opening 154 to increase resistance to tipping, or removed from the hollow interior 148 to reduce weight. A post 164 which in the illustrated example is substantially identical to the post 14 extends upwardly from the base 146. A vial support 166 which in the illustrated example is substantially identical to the vial support 16 is disposed adjacent to the upper end 168 of the post 164. A finger flange support 170 is disposed on an intermediate portion 172 of the post 164.

Although the illustrated example of the base 146 shows a side-opening door, a door may be provided on the top or bottom. Alternatively, individual weight-receiving openings may be provided in the top surface for each individual weight that is provided with the fixture. Although a round base is illustrated, any generally planer, substantially horizontal shape may be used for the base.

The components of each of the illustrated examples of a fixture for supporting a hypodermic syringe may be interchanged with each other to produce any desired combination of features. For example, any of the bases 12, 146 may be utilized with any of the fixtures 10, 74, 92, or 144. Similarly, any of the fixtures 10, 74, 92, or 144 may utilize a fixed finger flange support 20, a plurality of finger flange supports 84, 86, or a movable finger flange support 100, 120. The magnifier 112 may be used with any of the fixtures 10, 74, 92, or 144.

Although the illustrated examples include vertical posts and holds the vial in a top-down position, other examples may orient the vial and hypodermic syringe into any position that some may find to be convenient for filling the hypodermic syringe. The vial and hypodermic syringe may be held in a vertical position with the vial top facing up, in a horizontal position, or in any angled position without departing from the invention. As another alternative, some examples may include a vial support and finger flange support attached directly to a base without a vertical post. The fixture support structure may take a variety of forms as long as it holds the vial The present invention therefore provides a fixture for filling a hypodermic syringe. The fixture provides a means of holding the medication vial in a hands-free manner, as well as a means of supporting the syringe during filling. The fixture is simple to use, and facilitates the use of hypodermic syringes by patients and patient caregivers with diminished physical abilities. Some examples may include a magnifier that is positioned to facilitate reading the indicia on the barrel of the syringe.

A variety of modifications to the above-described embodiments will be apparent to those skilled in the art from this disclosure. Thus, the invention may be embodied in other specific forms without departing from the spirit or essential attributes thereof. The particular embodiments disclosed are meant to be illustrative only and not limiting as to the scope of the invention. The appended claims, rather than to the foregoing specification, should be referenced to indicate the scope of the invention.

What is claimed is:

1. A fixture for supporting a hypodermic needle and vial, the fixture comprising:
    a fixture support;
    a vial support having a support arm extending from the fixture support, the support arm defining a first vial support surface and a second vial support surface, the second vial support surface being angled with respect to the first vial support surface, the vial support including a vial securing elastomeric band pivotally secured to the support arm, the elastomeric band pivoting with respect to the support arm to selectively secure the hypodermic needle against either the first vial support surface or the second vial support surface;
    a finger flange support extending from the fixture support, the finger flange support being substantially coplanar with the vial support;
    whereby a vial may be secured by elastomeric tension provided by the elastomeric band to the vial support, a hypodermic syringe may be inserted into the vial, a plunger side surface of a finger flange on a barrel of the hypodermic syringe may be placed into contact with the finger flange support, and the finger flange support resists movement of the barrel while a plunger of the hypodermic syringe is withdrawn.

2. The fixture according to claim 1, wherein the fixture support includes a base and a post extending from the base.

3. The fixture according to claim 2, wherein the base includes weights.

4. The fixture according to claim 3, wherein the weights are removable.

5. The fixture according to claim 2, wherein each of the vial support and finger flange support are attached to the post.

6. The fixture according to claim 1, wherein:
the support arm defines a slot; and
the elastomeric band is held within the slot.

7. The fixture according to claim 1, wherein the fixture support includes weights.

8. The fixture according to claim 7, wherein the weights are removable.

9. The fixture according to claim 1, wherein:
the support arm defines an upper surface and an end surface;
the upper surface is the first vial support surface; and
the end surface is the second vial support surface.

10. A method of filling a hypodermic syringe, comprising:
providing a fixture, comprising:
- a fixture support;
- a vial support having a support arm extending from the fixture support, the support arm having a first vial support surface on an upper surface of the support atm and a second vial support surface on an end surface of the support arm, the vial support including a vial securing elastomeric band pivotally secured to the support arm;
- a finger flange support extending from the fixture support, the finger flange support being substantially coplanar with the vial support;

using the elastomeric hand to provide elastomeric tension to secure a vial against the first vial support surface, the vial having a top and containing medication;

inserting a needle of a hypodermic syringe into the top of the vial;

moving the vial to a position wherein the vial is secured against the second vial support surface;

placing a plunger side surface of a finger flange disposed on a barrel of the hypodermic syringe against the finger flange support; and withdrawing a plunger of the hypodermic syringe.

\* \* \* \* \*